(12) United States Patent
Ye et al.

(10) Patent No.: US 12,360,093 B2
(45) Date of Patent: *Jul. 15, 2025

(54) METHOD AND APPARATUS FOR PULSE GAS DELIVERY WITH CONCENTRATION MEASUREMENT

(71) Applicant: MKS Instruments, Inc., Andover, MA (US)

(72) Inventors: Hongke Ye, Andover, MA (US); Vidi Saptari, Andover, MA (US); Junhua Ding, Andover, MA (US)

(73) Assignee: MKS Instruments, Inc., Andover, MA (US)

( * ) Notice: Subject to any disclaimer, the term of this patent is extended or adjusted under 35 U.S.C. 154(b) by 385 days.

This patent is subject to a terminal disclaimer.

(21) Appl. No.: 17/757,902

(22) PCT Filed: Jan. 11, 2021

(86) PCT No.: PCT/US2021/012924
§ 371 (c)(1),
(2) Date: Jun. 23, 2022

(87) PCT Pub. No.: WO2021/146132
PCT Pub. Date: Jul. 22, 2021

(65) Prior Publication Data
US 2023/0031118 A1    Feb. 2, 2023

Related U.S. Application Data

(63) Continuation-in-part of application No. 16/742,172, filed on Jan. 14, 2020, now Pat. No. 11,513,108.

(51) Int. Cl.
*G01N 33/00* (2006.01)
*G01F 1/76* (2006.01)
(Continued)

(52) U.S. Cl.
CPC .......... *G01N 33/0067* (2013.01); *G01F 1/76* (2013.01); *G01N 33/0073* (2013.01);
(Continued)

(58) Field of Classification Search
CPC .. G01N 33/0067; G01N 33/0073; G01F 1/76; G01F 15/005; H01L 21/67253;
(Continued)

(56) References Cited

U.S. PATENT DOCUMENTS

| 5,501,893 A | 3/1996 | Laermer et al. |
| 6,284,148 B1 | 9/2001 | Laermer et al. |

(Continued)

FOREIGN PATENT DOCUMENTS

| CN | 101023199 A | 8/2007 |
| CN | 102791906 A | 11/2012 |

(Continued)

OTHER PUBLICATIONS https://controlguru.com/sample-time-is-a-fundamental-design-and-tuning-specification/, 2015 (Year: 2015).*

(Continued)

*Primary Examiner* — Timothy P Graves
(74) *Attorney, Agent, or Firm* — Hamilton, Brook, Smith & Reynolds, P.C.

(57) ABSTRACT

A system and method provides a more precise mole delivery amount of a process gas, for each pulse of a pulse gas delivery, by measuring a concentration of the process gas and controlling the amount of gas mixture delivered in a pulse of gas flow based on the received concentration of the process gas. The control of mole delivery amount for each pulse can be achieved by adjusting flow setpoint, pulse duration, or both.

30 Claims, 8 Drawing Sheets

(51) Int. Cl.
*G01F 15/00* (2006.01)
*G05D 11/13* (2006.01)
*H01L 21/67* (2006.01)

(52) U.S. Cl.
CPC ......... *G05D 11/138* (2013.01); *G05D 11/139* (2013.01); *G01F 15/005* (2013.01); *H01L 21/67253* (2013.01)

(58) Field of Classification Search
CPC .... G05D 11/133; G05D 7/0694; G05D 21/02; G05D 11/138; G05D 11/139; H01J 37/3299; H01J 37/32981; H01J 37/32449; C23C 16/52; C23C 16/45561; C23C 16/45544; C23C 16/448
See application file for complete search history.

(56) References Cited

U.S. PATENT DOCUMENTS

| | | |
|---|---|---|
| 6,531,068 B2 | 3/2003 | Laermer et al. |
| 7,615,120 B2 | 11/2009 | Shajii et al. |
| 7,628,860 B2 | 12/2009 | Shajii et al. |
| 7,735,452 B2 | 6/2010 | Spartz |
| 7,829,353 B2 | 11/2010 | Shajii et al. |
| 10,351,953 B2 | 7/2019 | Qian et al. |
| 10,353,408 B2 | 7/2019 | Ding et al. |
| 11,513,108 B2 | 11/2022 | Ye et al. |
| 2004/0015300 A1 | 1/2004 | Ganguli et al. |
| 2005/0095859 A1* | 5/2005 | Chen ............... C23C 16/52 438/689 |
| 2007/0022951 A1 | 2/2007 | Spartz |
| 2007/0039550 A1 | 2/2007 | Shajii et al. |
| 2010/0178423 A1 | 7/2010 | Shimizu et al. |
| 2011/0174219 A1 | 7/2011 | Meneghini |
| 2012/0216888 A1 | 8/2012 | Ding et al. |
| 2014/0190571 A1 | 7/2014 | Ding et al. |
| 2018/0258530 A1 | 9/2018 | Sakaguchi et al. |
| 2019/0177850 A1 | 6/2019 | Shimizu |
| 2019/0203358 A1 | 7/2019 | Babayan et al. |
| 2019/0243392 A1 | 8/2019 | Ding et al. |
| 2019/0265218 A1 | 8/2019 | Albright et al. |
| 2019/0279888 A1 | 9/2019 | Gopalakrishnan et al. |
| 2021/0215655 A1 | 7/2021 | Ye et al. |

FOREIGN PATENT DOCUMENTS

| | | | |
|---|---|---|---|
| CN | 103608486 A | 2/2014 | |
| JP | 2006-222133 A | 8/2006 | |
| JP | 2013-249511 A | 12/2013 | |
| WO | WO-2007008438 A2 * | 1/2007 | ....... C23C 16/45523 |
| WO | 2021146132 A1 | 7/2021 | |

OTHER PUBLICATIONS

J. Ding, M. L'Bassi, J. Schwartz and W. Cole, "Pulse gas delivery mass flow controllers for TSV applications," 2016 China Semiconductor Technology International Conference (CSTIC), 2016, pp. 1-3, doi: 10.1109/CSTIC.2016.7464085. (Year: 2016).*

International Search Report and Written Opinion for International Application No. PCT/US2021/012924, entitled "Method and Apparatus for Pulse Gas Delivery With Concentration Measurement," Dated: May 20, 2021.

J. Ding, M. L'Bassi, J. Schwartz and W. Cole, "Pulse gas delivery mass flow controllers for TSV applications," 2016 China Semiconductor Technology International Conference (CSTIC), 2016, pp. 1-3, doi: 10.1109/CSTIC.2016.7464085 (2016).

Non Final Office Action for U.S. Appl. No. 16/742,172, entitled "Method and Apparatus for Pulse Gas Delivery with Concentration Measurement," dated Sep. 28, 2021.

Non Final Office Action for U.S. Appl. No. 16/742,172, entitled "Method and Apparatus for Pulse Gas Delivery with Concentration Measurement," dated Jun. 7, 2022.

Final Office Action for U.S. Appl. No. 16/742,172, entitled "Method and Apparatus for Pulse Gas Delivery with Concentration Measurement," dated Jan. 20, 2022.

Advisory Action for U.S. Appl. No. 16/742,172, entitled "Method and Apparatus for Pulse Gas Delivery with Concentration Measurement," dated May 10, 2022.

Interview Summary for U.S. Appl. No. 16/742,172, entitled "Method and Apparatus for Pulse Gas Delivery with Concentration Measurement," dated Apr. 12, 2022.

Notice of Allowance and Fees Due for U.S. Appl. No. 16/742,172, entitled "Method and Apparatus for Pulse Gas Delivery with Concentration Measurement," dated Sep. 28, 2022.

International Preliminary Report on Patentability and Written Opinion for International Application No. PCT/US2021/012924, entitled "Method and Apparatus for Pulse Gas Delivery with Concentration Measurement," mailed on Jul. 28, 2022.

* cited by examiner

METHOD AND APPARATUS FOR PULSE GAS DELIVERY WITH CONCENTRATION MEASUREMENT

RELATED APPLICATION

This application is the U.S. National Stage of International Application No. PCT/US2021/012924, filed Jan. 11, 2021, which designates the U.S., published in English, and claims priority under 35 U.S.C. § 119 or 365(c) to, and which is a continuation-in-part of, U.S. application Ser. No. 16/742,172, filed Jan. 14, 2020. The entire teachings of the above applications are incorporated herein by reference.

BACKGROUND

For many processes that involve a pulsed delivery of gas, such as Atomic Layer Deposition (ALD) processes and Atomic Layer Etch (ALE) processes, a precursor or other process gas is mixed with a carrier gas. Because of the way in which the process gas is typically generated, the concentration of the process gas may vary during the process, for example as the output of a chemical reaction generating the process gas varies over time. Nevertheless, it is important to provide precise mole delivery amount of the process gas to the process chamber.

However, existing pulse gas delivery devices can only guarantee the total mole amount in each pulse, where the total mole amount includes both the process gas and the carrier gas, and the mole amount of the process gas in each pulse may therefore vary. There is, therefore, an ongoing need for more precise mole delivery amounts of process gases in pulsed gas mixtures.

SUMMARY

A method and apparatus for pulse gas delivery with concentration measurement is disclosed. The method and apparatus provides a more precise mole delivery amount of a process gas, for each pulse of a pulse gas delivery, by measuring a concentration of the process gas and controlling the amount of gas mixture delivered in a pulse of gas flow based on the received concentration of the process gas. The control of mole delivery amount for each pulse can be achieved by adjusting flow setpoint, pulse duration, or both.

A pulse gas control system comprises a gas concentration measurement system configured to measure a concentration of a process gas in a gas mixture. The pulse gas delivery system is configured to sense flow of the gas mixture and control flow of the gas mixture. The system receives the concentration of the process gas in the gas mixture, measured by the gas concentration measurement system, and controls an amount of gas mixture delivered in a pulse of gas flow based on the received concentration of the process gas to control a mole amount of the process gas delivered to a process chamber in each pulse.

The pulse gas delivery system may be configured to adjust a flow setpoint of the gas mixture during the pulse, and the adjustment may be based on the received concentration of the process gas. The pulse gas delivery system may set an initial target flow setpoint of the gas mixture in inverse proportion to the received concentration of the process gas. The initial target flow setpoint may be set in proportion to a process gas mole delivery per pulse setpoint divided by a product of a pulse duration period multiplied by the received concentration of the process gas. The pulse gas delivery system may adjust the flow setpoint, during a pulse duration period, based on a changed measurement of the process gas concentration during the pulse duration period. The adjustment of the flow setpoint may be based on a relationship:

$$Q_{sp}(t) = \frac{k \cdot M_{sp} - \int_{t_0}^{t} Q_m(t)C(t)dt}{(\Delta t - (t - t_0)) \cdot C(t)}$$

where $Q_{sp}(t)$ is the flow setpoint, k is a mole to flow unit conversion constant, $M_{sp}$ is a process gas mole delivery per pulse setpoint, $Q_m(t)$ is a measured flow rate of the pulse gas delivery system, C(t) is the received process gas concentration, $\Delta t$ is the pulse duration period, t is a current time, and $t_0$ is an initial time of the pulse duration period. The pulse gas delivery system may adjust the flow setpoint over time during the pulse duration period until the pulse duration period is complete. A constant pulse duration may be maintained while adjusting the flow setpoint.

The gas concentration measurement system may comprise an optical gas sensor, a surface acoustic wave device, an ultrasound sensor, a mass spectrometer or a thermal conductive detector. The gas concentration measurement system may be arranged in series between a source of the gas mixture and the pulse gas delivery system, to receive the gas mixture from a source and to provide the gas mixture to the pulse gas delivery system. It may be arranged to receive a sample of the gas mixture from a sample line that samples a gas flow of the gas mixture from a source to the pulse gas delivery system. The process chamber to which the pulse gas delivery system is configured to deliver the process gas may be one of: an Atomic Layer Deposition (ALD) process, an Atomic Layer Etch (ALE) process, a Through Silicon Via (TSV) process, a pulsed deep reactive ion etch (DRIE) process, a plasma enhanced chemical vapor deposition (CVD) process and a plasma enhanced etching process.

The pulse gas delivery system may be configured to adjust a flow setpoint of the gas mixture during the pulse. The pulse gas delivery system may be configured to adjust a pulse duration used to deliver the gas mixture to the process chamber; and may be configured to adjust the pulse duration by ending the pulse duration when a total mole amount of process gas delivered is greater than or equal to a process gas mole delivery per pulse setpoint. The pulse gas delivery system may be configured to adjust both a flow setpoint of the gas mixture, and the pulse duration during the pulse.

The pulse gas delivery system may be configured to receive the concentration of the process gas in the gas mixture at an update rate that is at least ten times a pulse frequency that corresponds to a pulse duration period of the pulse gas delivery system. The system may comprise a heater configured to maintain at least part of the flow of the gas mixture comprising the process gas at an elevated temperature. The pulse gas delivery system may be configured to control the heater to maintain a substantially constant elevated temperature of the process gas along at least part of the flow of the gas mixture between a source and the process chamber.

A method of controlling a pulse gas delivery system comprises measuring a concentration of a process gas in a gas mixture; with the pulse gas delivery system, receiving the concentration of the process gas in the gas mixture; and controlling an amount of gas mixture delivered in a pulse of gas flow by the pulse gas delivery system based on the received concentration of the process gas to control a mole amount of the process gas delivered to a process chamber in each pulse.

The method may comprise adjusting a flow setpoint of the gas mixture during the pulse. The flow setpoint of the gas mixture may be adjusted based on the received concentration of the process gas. An initial target flow setpoint of the gas mixture may be set in inverse proportion to the received concentration of the process gas. The initial target flow setpoint may be set in proportion to a process gas mole delivery per pulse setpoint divided by a product of a pulse duration period multiplied by the received concentration of the process gas. The method may comprise adjusting the flow setpoint, during a pulse duration period, based on a changed measurement of the process gas concentration during the pulse duration period. The method may comprise adjusting the flow setpoint based on a relationship:

$$Q_{sp}(t) = \frac{k \cdot M_{sp} - \int_{t_0}^{t} Q_m(t)C(t)dt}{(\Delta t - (t - t_0)) \cdot C(t)}$$

where $Q_{sp}(t)$ is the flow setpoint, k is a mole to flow unit conversion constant, $M_{sp}$ is a process gas mole delivery per pulse setpoint, $Q_m(t)$ is a measured flow rate of the pulse gas delivery system, C(t) is the received process gas concentration, $\Delta t$ is the pulse duration period, t is a current time, and $t_0$ is an initial time of the pulse duration period. The method may comprise adjusting the flow setpoint over time during the pulse duration period until the pulse duration period is complete. The method may comprise maintaining a constant pulse duration while adjusting the flow setpoint.

The method may comprise measuring the concentration of the process gas in the gas mixture using an optical gas sensor, a surface acoustic wave device, an ultrasound sensor, a mass spectrometer or a thermal conductive detector. The pulse gas delivery system may be used to deliver the process gas to one of: an Atomic Layer Deposition (ALD) process, an Atomic Layer Etch (ALE) process, a Through Silicon Via (TSV) process, a pulsed deep reactive ion etch (DRIE) process, a plasma enhanced chemical vapor deposition (CVD) process and a plasma enhanced etching process. The method may comprise adjusting a flow setpoint of the gas mixture during the pulse. The method may comprise adjusting a pulse duration used to deliver the gas mixture to the process chamber; and may comprise adjusting the pulse duration by ending the pulse duration when a total mole amount of process gas delivered is greater than or equal to a process gas mole delivery per pulse setpoint. The method may comprise adjusting a flow setpoint of the gas mixture during the pulse and adjusting the pulse duration.

The method may comprise receiving the concentration of the process gas in the gas mixture at an update rate that is at least ten times a pulse frequency that corresponds to a pulse duration period of the pulse gas delivery system. The method may comprise using a heater to maintain at least part of the flow of the gas mixture comprising the process gas at an elevated temperature; and may comprise controlling the heater to maintain a substantially constant elevated temperature of the process gas along at least part of the flow of the gas mixture between a source and the process chamber.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

In previous gas delivery systems, precursor gases or other process gases are typically generated by a chemical or physical process that is ongoing during gas delivery, such as by evaporating a liquid or solid. For example, a carrier gas such as nitrogen can be flowed through an ampoule containing a precursor substance, to produce a vapor, which bubbles out of the ampoule and contains a mixture of the carrier gas and the precursor gas. The ampoule is heated to a high temperature to vaporize the solid or liquid precursor, so the rate of vaporization is often highly dependent on the pressure, temperature and surface area involved in the reaction. The rate of the chemical reaction or physical process that is used to generate the process gas can vary widely during the production of the process gas.

Because of this varying rate of production of the process gas, previous pulse gas delivery systems could often deliver mole amounts of the process gas that varied widely from pulse to pulse, even where the total amount of the combination of the process gas and the carrier gas was kept relatively constant. Such variation of the process gas amount, however, can produce a great variation in the result of the manufacturing process that the process gas is used in, for example by producing a varying thickness of layers deposited on a surface in an Atomic Layer Deposition (ALD) process.

In order to address these and other drawbacks of previous systems, concentration measurement is used to provide a precise mole delivery of gas mixtures in a pulse gas delivery system, as will be described further herein.

Figure 1A:
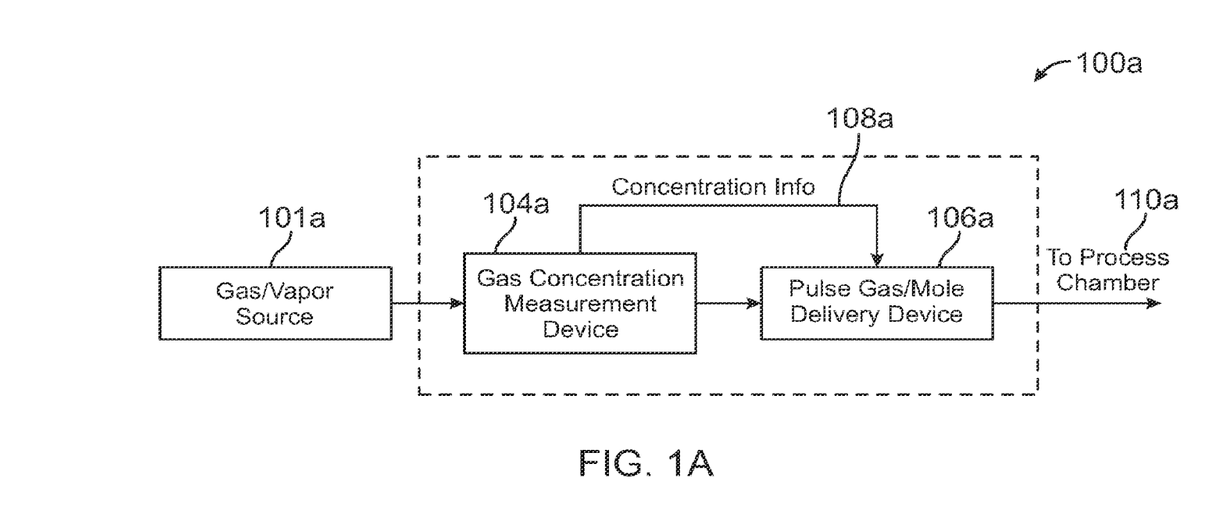
FIG. 1A is a schematic block diagram of a pulse gas control system using concentration measurement, in an in-line arrangement, in accordance with an embodiment of the invention.

FIG. 1A is a schematic block diagram of a pulse gas control system 100a using concentration measurement, in an in-line arrangement, in accordance with an embodiment of the invention. A gas source 101a flows a gas mixture of a process gas with a carrier gas into the system, and the gas mixture flows through a gas concentration measurement system 104a and a pulse gas delivery system 106a. In the embodiment of FIG. 1A, the gas concentration measurement system 104a and pulse gas delivery system 106a are in an "in-line," or series flow, arrangement. In this embodiment, the gas concentration measurement system 104a is arranged in series between the source 101a of the gas mixture and the pulse gas delivery system 106a, to receive the gas mixture from the source 101a and to provide the gas mixture to the pulse gas delivery system 106a. It will be appreciated that other flow arrangements can be used, for example as in FIG. 1B. In FIG. 1A, the pulse gas delivery system 106a senses and controls flow of the gas mixture. The gas concentration measurement system 104a measures the concentration 108a of the process gas in the gas mixture. The pulse gas delivery system 106a receives the concentration 108a of the process gas, measured by the gas concentration measurement system 104a, and controls an amount of gas mixture delivered in a pulse of gas flow based on the received concentration 108a of the process gas, to control a mole amount of the process gas delivered 110a to a process chamber in each pulse.

Figure 1B:
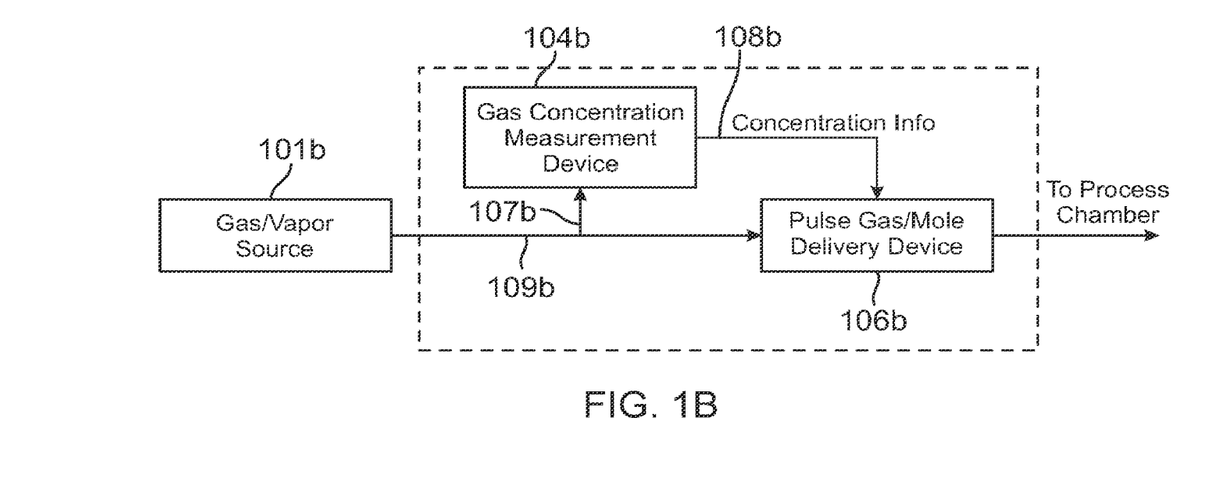
FIG. 1B is a schematic block diagram of a pulse gas control system using concentration measurement, in a sample line arrangement, in accordance with an embodiment of the invention.

FIG. 1B is a schematic block diagram of a pulse gas control system using concentration measurement, in a sample line arrangement, in accordance with an embodiment of the invention. In this embodiment, the gas concentration measurement system 104b is arranged to receive a sample of the gas mixture from a sample line 107b that samples a gas flow of the gas mixture from the source 101b to the pulse gas delivery system 106b. The gas source 101b flows the gas mixture into the pulse gas delivery system 106b, and the gas concentration measurement system 104b receives the sample of the gas mixture from the sample line 107b, which branches off the flow line 109b by which the gas source 101b flows the gas mixture into the pulse gas delivery system 106b. The gas concentration measurement system 104b is thus able to measure the concentration 108b of the process gas in the gas mixture, and provide it to the pulse gas delivery system 106b. The system is otherwise analogous to that of FIG. 1A.

Using the gas concentration measurement system 104a/104b, the system of FIGS. 1A and 1B obtains the concentration 108a/108b of the precursor or other process gas in the gas mixture, which is fed into the pulse gas delivery system 106a/106b. The pulse gas mole delivery device 106a/106b adjusts the total mole amount of the gas mixture—including both the process gas and the carrier gas—for each pulse gas mole delivery, such that the mole amount of the process gas is maintained as a constant. The total mole amount adjustment of the gas mixture can be achieved by adjusting flow setpoint, pulse duration or both. In some embodiments, the system can change the flow setpoint only, without changing the pulse duration, so that the pulse gas delivery is synchronized with other instruments in the manufacturing process, such as with the radio frequency (RF) generation in the process chamber.

The pulse gas delivery system 106a/106b can, for example, be a pulse Mass Flow Controller (MFC) or mole delivery device. For example, the pulse gas delivery system 106a/106b can be any of the pulse gas delivery systems taught in U.S. Pat. No. 10,353,408 B2 of Ding et al., U.S. Pat. No. 7,628,860 B2 of Shajii et al., U.S. Pat. No. 7,615,120 B2 of Shajii et al., U.S. Pat. No. 7,829,353 B2 of Shajii et al., and U.S. Patent App. Pub. Nos. 2014/0190571 of Ding et al. and 2019/0243392 A1 of Ding et al., the teachings of each of which are incorporated by reference in their entirety.

The gas concentration measurement system 104a/104b can, for example, be or include an optical gas sensor, a surface acoustic wave device, an ultrasound sensor, a mass spectrometer or a thermal conductive detector. For example, an infrared (IR) absorption based gas sensor, such as a Tunable Filter Spectrometer (TFS), Nondispersive Infrared (NDIR) sensor, or Fourier-Transform Infrared Spectrometer (FTIR) sensor, can be used. Infrared absorption based gas sensors have good sensitivity and selectivity, their measurement is non-invasive, and they can be arranged in-line to the delivery system. However, other concentration measurement methods, such as other optical gas sensors, surface acoustic wave (SAW) sensors, ultrasound sensors, mass spectrometry, and thermal conductive detectors, can also be used.

The process chamber to which the pulse gas delivery system is configured to deliver 110a the process gas can, for example, be one of: an Atomic Layer Deposition (ALD) process, an Atomic Layer Etch (ALE) process, a Through Silicon Via (TSV) process, a pulsed deep reactive ion etch (DRIE) process, a plasma enhanced chemical vapor deposition (CVD) process a plasma enhanced etching process, or any process requiring a pulsed gas mixture. The process can, for example, be part of a semiconductor manufacturing process, but can also be used in other processes. As used herein, a pulsed deep reactive ion etch (DRIE) process is, for example, a highly anisotropic etch process used to create deep penetration, steep-sided holes and trenches in wafers and other substrates, typically with a high aspect ratio. In one example, the DRIE process is a pulsed or time-multiplexed etching process, such as any of those taught in U.S. Pat. No. 5,501,893 A of Laermer et al., U.S. Pat. No. 6,531,068 B2 of Laermer et al., and U.S. Pat. No. 6,284,148 B1 of Laermer et al., the teachings of each of which are incorporated by reference in their entirety.

Figure 2:
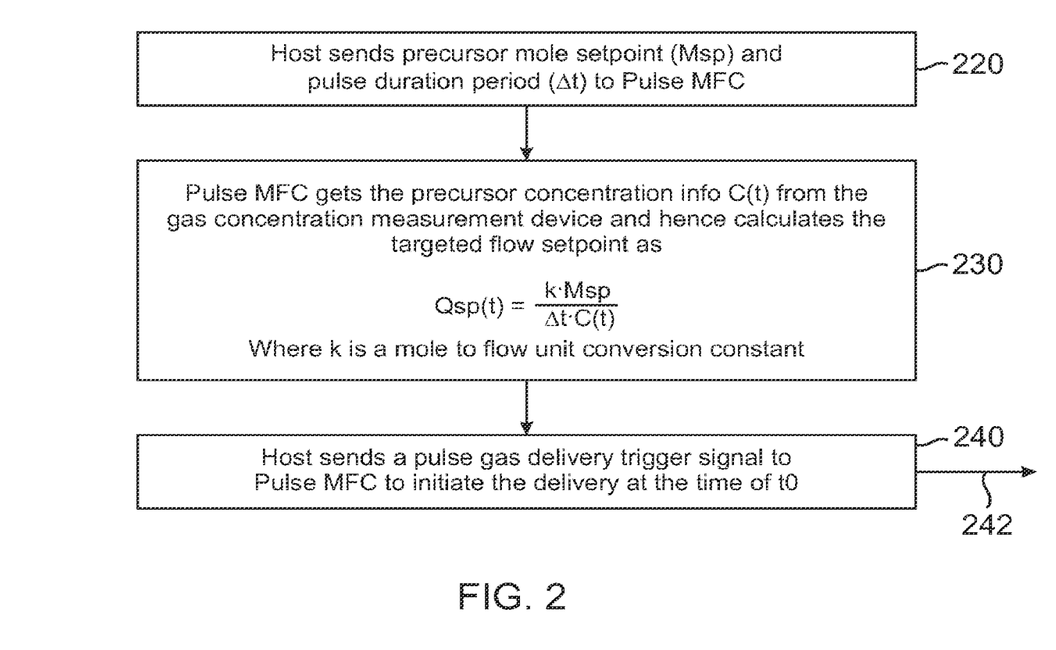
FIGS. 2 and 3 are schematic block diagrams of a process of controlling a pulse gas delivery system by adjusting a flow setpoint of the gas mixture during the pulse in accordance with an embodiment of the invention.
Figure 3:
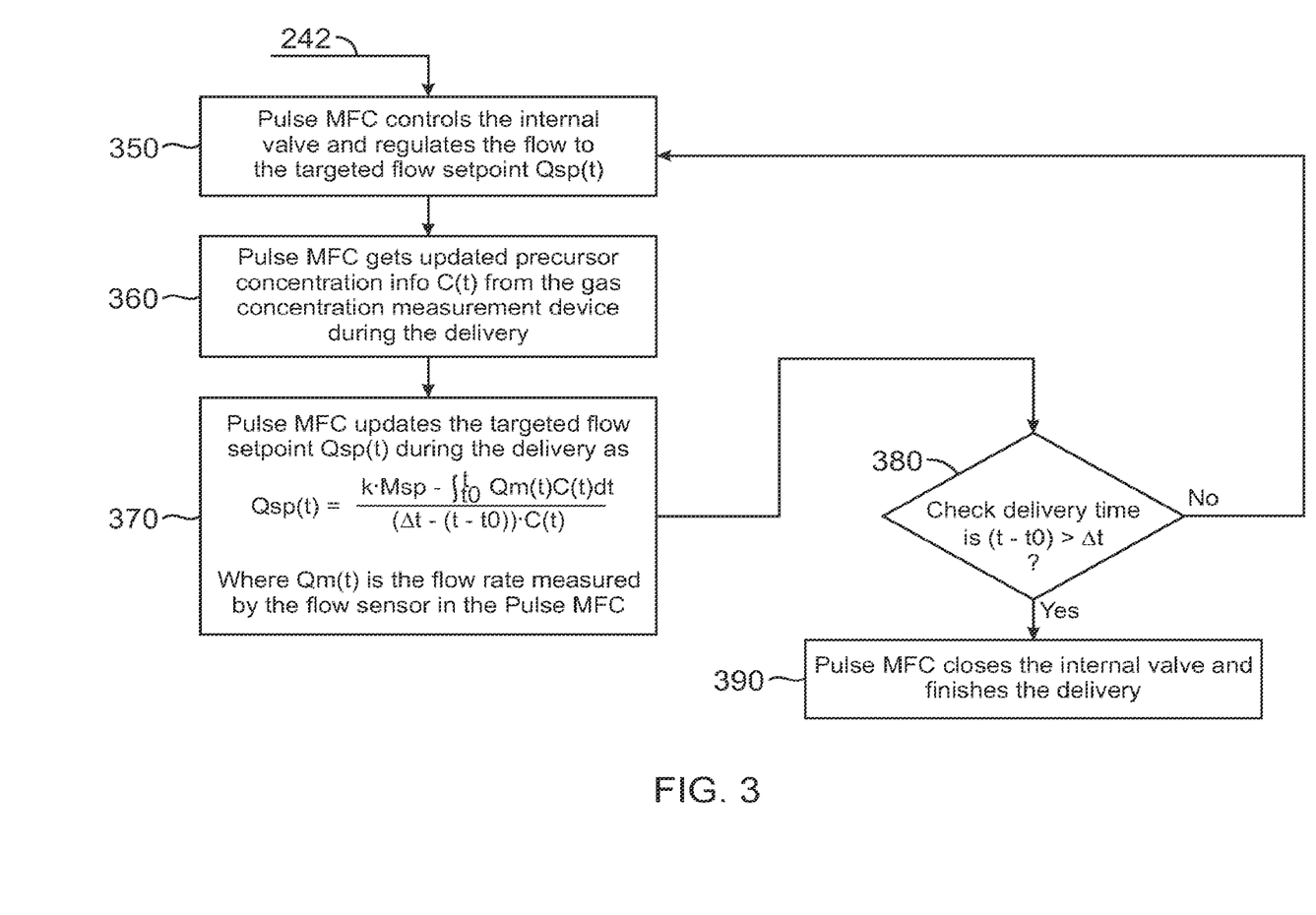

FIGS. 2 and 3 are schematic block diagrams of a process of controlling a pulse gas delivery system by adjusting a flow setpoint of the gas mixture during the pulse, in accordance with an embodiment of the invention. In the embodiments of FIGS. 2 and 3, the pulse gas delivery system adjusts a flow setpoint of the gas mixture during the pulse, in order to achieve a precise mole amount of the process gas in each pulse. The pulse gas delivery system can maintain a constant pulse duration while adjusting the flow setpoint. However, it will be appreciated that the pulse gas delivery system can also adjust the pulse duration used to deliver the gas mixture to the process chamber; or can both adjust the flow setpoint of the gas mixture during the pulse and adjust the pulse duration (see FIGS. 7 and 8, for example).

In the process of FIG. 2, the host controller (see 505 of FIG. 5, which can, for example, be implemented as a host processor of a tool in which the pulse gas delivery system is used) sends 220 a precursor (or other process gas) mole setpoint ($M_{sp}$) and a pulse duration period ($\Delta t$) to the pulse gas delivery system (see 106a/106b of FIGS. 1A and 1B), such as a pulse mass flow controller (MFC). (The mole setpoint and pulse duration can be in signals 515 sent to and from the host controller 505 of FIG. 5). The mole setpoint can, for example, be on the order of about 100 micromoles per pulse, although it will be appreciated that other mole amounts can be used. The pulse gas delivery system can set 230 an initial target flow setpoint of the gas mixture in inverse proportion to the received concentration of the process gas. For example, as shown in step 230 of FIG. 2, the pulse gas delivery system can set the initial target flow setpoint, $Q_{sp}(t)$, in proportion (for example, based on a proportionality constant, k) to a process gas mole delivery per pulse setpoint ($M_{sp}$) divided by a product of a pulse duration period ($\Delta t$) multiplied by the received concentration of the process gas, C(t), which is received from the gas concentration measurement device (see 104a/104b of FIGS. 1A and 1B). The host controller (see 505 of FIG. 5) then sends 240 a pulse gas delivery trigger signal (which can be in signals 515 sent to and from the host controller 505 of FIG. 5) to the pulse gas delivery system (see 106a/106b of FIGS. 1A and 1B) to initiate the delivery at the initial time of the pulse duration period ($t_0$). The process continues 242 as shown in FIG. 3.

In the technique of FIGS. 2 and 3, the pulse gas delivery system adjusts the flow setpoint of the gas mixture based on the received concentration of the process gas. Continuing from the process of FIG. 2 at 242 in FIG. 3, the pulse gas delivery system (see 106a/106b of FIGS. 1A and 1B) regulates 350 its flow (for example by controlling an internal control valve 513 of FIG. 5) to the targeted flow setpoint, $Q_{sp}(t)$. The pulse gas delivery system (see 106a/106b of FIGS. 1A and 1B) adjusts the flow setpoint, $Q_{sp}(t)$, during a pulse duration period, based on a changed measurement of the process gas concentration during the pulse duration period. For example, at 360 in FIG. 3, the pulse gas delivery system obtains an updated precursor gas (or other process gas) concentration information, C(t), from the gas concentration measurement device (see 104a/104b of FIGS. 1A and 1B) during the delivery. The concentration information C(t) can be updated in real time based on a clock period of the host processor (505 of FIG. 5) or pulse mole amount control processor (see 511 of FIG. 5), or both, which can, in one example, be about 5 milliseconds, or another clock period. The update rate of the concentration information C(t) can be set in the manner discussed relative to FIG. 5, below. And next, for example, in 370 in FIG. 3, the pulse gas delivery system (106a/106b of FIGS. 1A and 1B) can adjust the flow setpoint based on a relationship:

$$Q_{sp}(t) = \frac{k \cdot M_{sp} - \int_{t_0}^{t} Q_m(t)C(t)dt}{(\Delta t - (t - t_0)) \cdot C(t)}$$

where $Q_{sp}(t)$ is the flow setpoint, k is a mole to flow unit conversion constant, $M_{sp}$ is a process gas mole delivery per pulse setpoint, $Q_m(t)$ is a measured flow rate of the pulse gas delivery system, C(t) is the received process gas concentration, $\Delta t$ is the pulse duration period, t is a current time, and $t_0$ is an initial time of the pulse duration period. The pulse gas delivery system (106a/106b of FIGS. 1A and 1B) can adjust the flow setpoint over time during the pulse duration period until the pulse duration period is complete. For example, in step 380 of FIG. 3, the system 106a/106b can check whether the delivery time, t, is greater than the pulse duration period ($\Delta t$) away from the initial time, that is, whether ($t-t_0$) is greater than $\Delta t$. If not, then the process repeats by regulating 350 the flow to the targeted flow setpoint, $Q_{sp}(t)$. If so, then the process completes the pulse gas delivery, as at 390, for example by having the pulse gas delivery system (106a/106b of FIGS. 1A and 1B) close an internal control valve (see 513 of FIG. 5) and finish the delivery of the gas pulse. In this way, the embodiment of FIGS. 2 and 3 is regularly updating the flow setpoint based on the updated process gas concentration information, during the pulse, so that the flow is increased as process gas concentration falls, and the flow is decreased as process gas concentration rises. This means that the total gas flow amount is changed, as the total flow is changed depending on the process gas concentration changes, but because the flow changes in an inverse manner to the process gas concentration, a controlled amount of the process gas is delivered in each pulse of the pulse gas delivery.

It will be appreciated that other techniques of flow setpoint can be used than those of FIGS. 2 and 3. For example, in another technique, C(t) in step 370 could be treated as a constant over the course of a pulse duration, on the theory that C(t) will change by small amounts over the course of each pulse duration, while still changing the flow setpoint $Q_{sp}(t)$ based on the changes in the measured flow rate $Q_m(t)$, which may change faster during the pulse duration.

Figure 7:
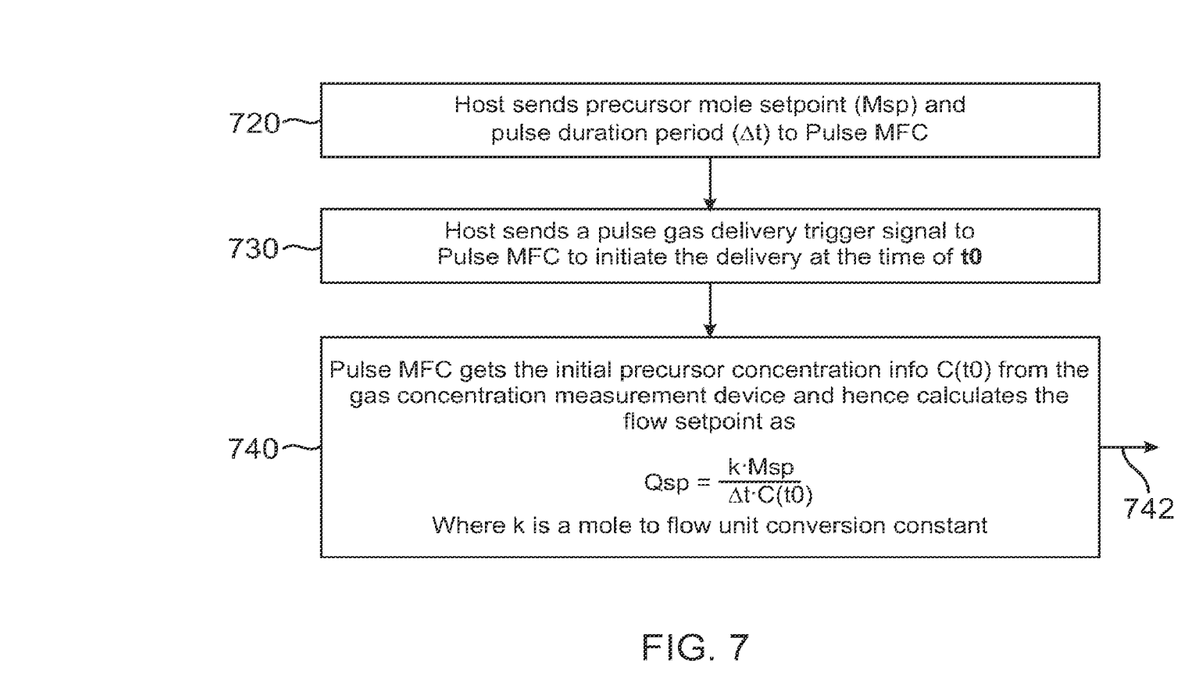
FIGS. 7 and 8 are schematic block diagrams of a process of controlling a pulse gas delivery system by adjusting a pulse duration used to deliver the gas mixture to the process chamber, in accordance with an embodiment of the invention.
Figure 8:
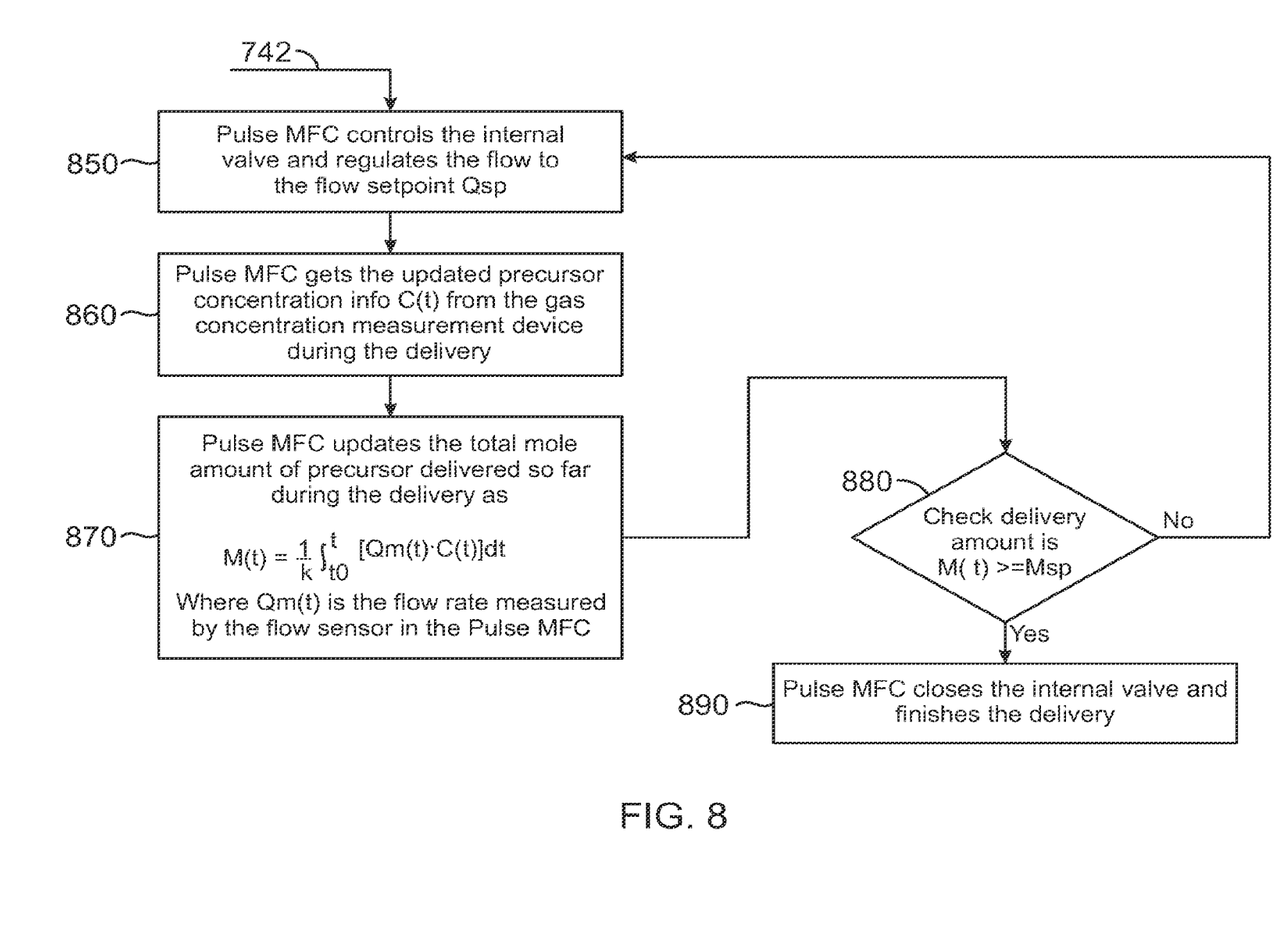

FIGS. 7 and 8 are schematic block diagrams of a process of controlling a pulse gas delivery system by adjusting the pulse duration period during the pulse in accordance with an embodiment of the invention. Although these figures show adjusting only the pulse duration period, it will also be appreciated that the method can include adjusting both the pulse duration period and the flow setpoint. In FIG. 7, the host controller (see 505 of FIG. 5) sends 720 a precursor (or other process gas) mole setpoint ($M_{sp}$) and a pulse duration period ($\Delta t$) to the pulse gas delivery system (see 106a/106b of FIGS. 1A and 1B), such as a pulse mass flow controller (MFC). The host controller (see 505 of FIG. 5) then sends 730 a pulse gas delivery trigger signal (which can be in signals 515 sent to and from the host controller 505 of FIG. 5) to the pulse gas delivery system (see 106a/106b of FIGS. 1A and 1B) to initiate the delivery at the initial time of the pulse duration period ($t_0$). The pulse gas delivery system, as shown in step 740 of FIG. 7, obtains the initial process gas concentration information 108a/108b, C(t0), from the gas concentration measurement device 104a/104b of FIG. 1 and calculates the flow setpoint as $$Qsp = \frac{k \cdot Msp}{\Delta t \cdot C(t0)}$$

The process continues 742 as shown in FIG. 8.

Continuing from the process of FIG. 7 at 742 in FIG. 8, the pulse gas delivery system (see 106a/106b of FIGS. 1A and 1B) regulates 850 its flow (for example by controlling an internal control valve 513 of FIG. 5) to the flow setpoint, $Q_{sp}$. The pulse gas delivery system (see 106a/106b of FIGS. 1A and 1B) monitors the total mole amount of the precursor gas delivered during the delivery. For example, at 860 in FIG. 8, the pulse gas delivery system obtains an updated precursor gas (or other process gas) concentration information, C(t), from the gas concentration measurement device (see 104a/104b of FIGS. 1A and 1B) during the delivery. Next, for example, in 870 in FIG. 8, the pulse gas delivery system (106a/106b of FIGS. 1A and 1B) can update the total mole amount of precursor gas delivered during the delivery as $$M(t) = \frac{1}{k} \int_{t0}^{t} [Qm(t) \cdot C(t)]dt$$

where Qm(t) is the flow rate measured by the flow sensor in the pulse gas delivery system. In step 880 of FIG. 8, the system 106a/106b can check whether the total mole amount of precursor gas delivered, i.e., M(t), is greater than or equal to the precursor mole setpoint Msp. If not, then the process repeats by regulating 850 the flow to the targeted flow setpoint, $Q_{sp}$, which in this embodiment is maintained as the same targeted flow setpoint, $Q_{sp}$, as was initially used. If so, then the process completes the pulse gas delivery, as at 890, for example by having the pulse gas delivery system (106a/106b of FIGS. 1A and 1B) close an internal control valve (see 513 of FIG. 5) and finish the delivery of the gas pulse. In this way, the embodiment of FIGS. 7 and 8 is regularly updating the pulse duration period or the pulse gas delivery time based on the updated process gas concentration information, during the delivery, so that the pulse duration is increased as process gas concentration falls, and the pulse duration is decreased as process gas concentration rises. It will be appreciated that the updating of the pulse duration period is achieved as a consequence of the pulse duration period being shorter when the total mole amount, M(t), reaches the precursor mole setpoint, Msp, in a shorter amount of time, and being longer when the total mole amount, M(t), reaches the precursor mole setpoint, Msp, in a longer amount of time. Thus, the technique of FIGS. 7 and 8 involves adjusting the pulse duration by ending the pulse duration when a total mole amount of process gas delivered is greater than or equal to a process gas mole delivery per pulse setpoint.

Figure 4:
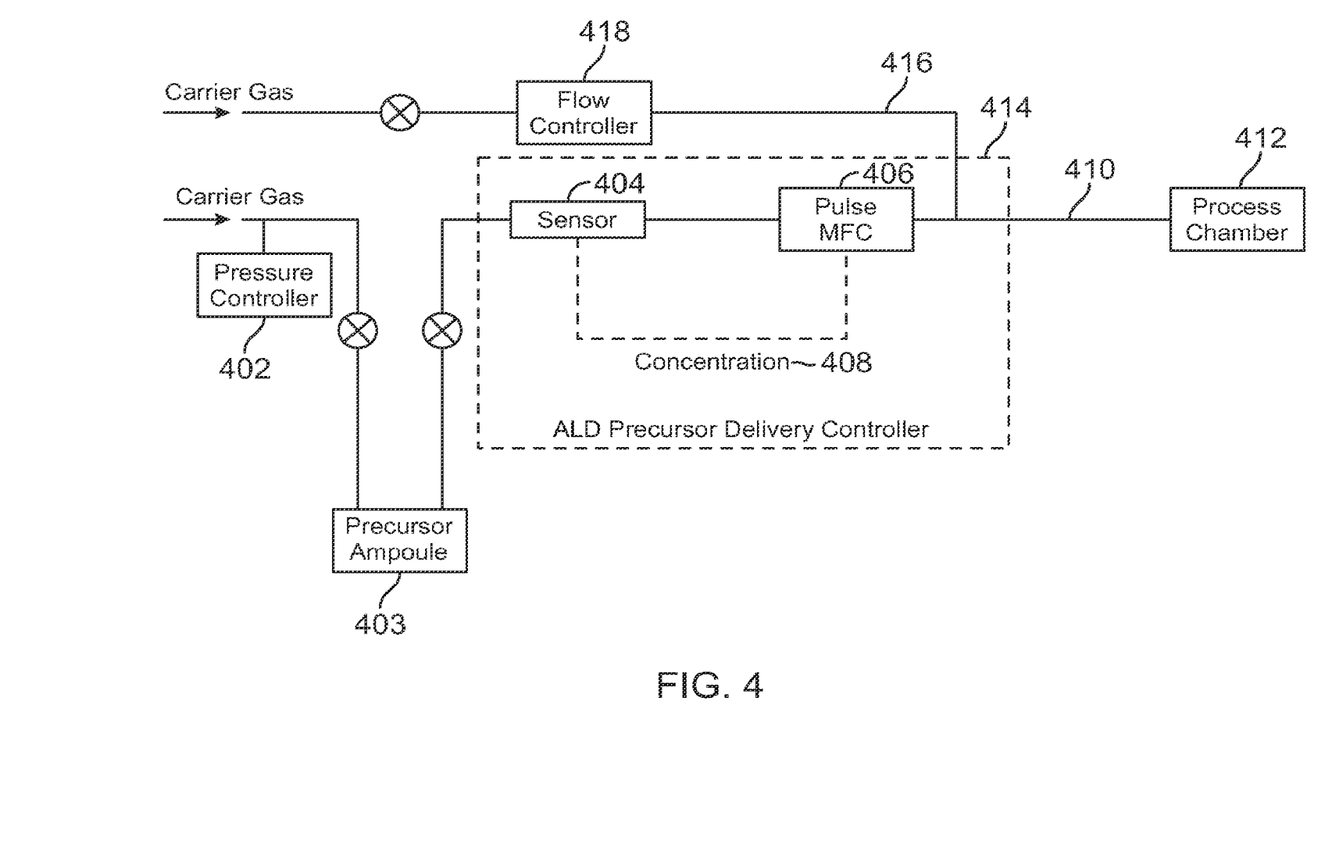
FIG. 4 is a schematic block diagram of a pulse gas control system using an additional carrier gas line in accordance with an embodiment of the invention.

FIG. 4 is a schematic block diagram of a pulse gas control system using an additional carrier gas line, in accordance with an embodiment of the invention. In this embodiment, there is shown a pressure controller 402 that controls flow of a carrier gas through a precursor (or other process gas generating) ampoule 403. A gas concentration measurement device 404 (for example, a sensor 404) provides concentration information 408 to the pulse gas delivery system 406 (for example, a pulse mass flow controller), and a precise mole amount of the process gas is then provided in each pulse to the process chamber 412. Here, the gas concentration measurement device 404 and pulse gas delivery system 406 are integrated together as an Atomic Layer Deposition (ALD) Precursor Delivery Controller 414, although it will be appreciated that the system can be used in other processes. In addition, in FIG. 4, a further carrier gas line 416 can be used to mix the pulse gas delivery 410 with an additional desired amount of carrier gas from carrier gas line 416, the flow of which can be controlled with its own carrier gas flow controller 418 (controlled, for example, by host controller 505 of FIG. 5). It will be appreciated that the additional carrier gas line 416 need not be used, and that other flow circuits can be added to the systems taught herein.

Figure 5:
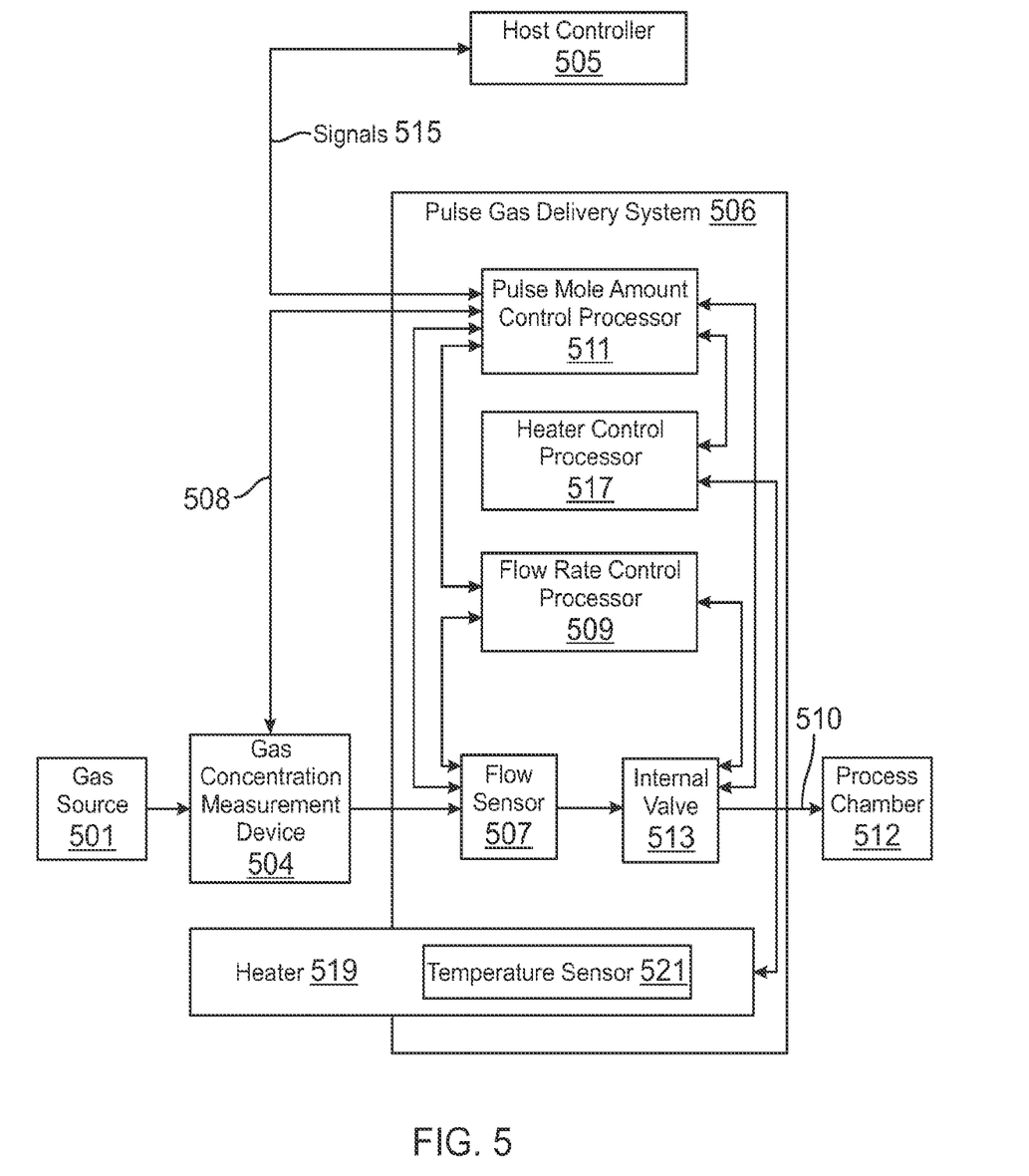
FIG. 5 is a schematic block diagram of a host controller interacting with a pulse gas delivery system in accordance with an embodiment of the invention.

FIG. 5 is a schematic block diagram of a host controller 505 interacting with a pulse gas delivery system 506 in accordance with an embodiment of the invention. In FIG. 5, a gas mixture flows from the gas source 501 through the gas concentration measurement device 504, to the pulse gas delivery system 506. The gas concentration measurement device 504 measures the concentration of the process gas in accordance with techniques taught herein, and provides a concentration signal 508 to a pulse mole amount control processor 511 of the pulse gas delivery system 506. The pulse mole amount control processor 511 can include suitable components (such as specially programmed application specific integrated circuits or a microprocessor) that are programmed to implement techniques taught herein based on the concentration signal 508 provided by the gas concentration measurement device 504, and to communicate with and control other components of the pulse gas delivery system 506. The pulse gas delivery system 506 also includes an internal control valve 513 to regulate flow. Upon completion of a pulse duration, the pulse gas delivery system 506 provides 510 a precise mole amount of the process gas in a pulse to the process chamber 512. The pulse gas delivery system 506 also includes a flow sensor 507 with which it senses flow, and a flow rate control processor 509, which uses separate, conventional techniques to control a measured flow rate, $Q_m$ to be as close as possible to a flow setpoint, $Q_{sp}$. The flow sensor may be a thermal flow sensor, differential pressure flow sensor or other sensor used in conventional mass flow controllers. In addition, the host controller 505 communicates via signals 515 to and from pulse mole amount control processor 511, to coordinate the control techniques taught herein implemented by pulse mole amount control processor 511 with the host tool. For example, signals 515 can include a mole setpoint, a pulse duration, and a pulse gas delivery trigger signal, provided by the host controller 505 to the pulse mole amount control processor 511.

The gas concentration measurement device 504 can send concentration signal 508, and the pulse gas delivery system 506 can receive concentration signal 508, with an update rate that is suitably faster than the pulse duration period ($\Delta t$) of the system. This update rate can effectively set the rate of updating of the feedback loop in the system, such as the loop in steps 350, 360, 370, and 380 of FIG. 3. The fast update rate can for example, help to ensure that the concentration is sensed at a rate that is sufficiently fast for the transition rates of temperatures and process gas changes in the system. In one example, it has been found useful to send the concentration signal 508, and update the feedback loop, with an update rate that is at least 10 times greater than the pulse frequency of the system. For example, a 200 millisecond pulse duration period has a 5 Hz frequency, and in that case, the update rate of the concentration signal 508 and the feedback loop (steps 350, 360, 370 and 380 of FIG. 3) should have a frequency of at least 50 Hz, that is, at least ten times faster than the pulse duration frequency. The update rate of the concentration signal 508 and of the feedback loop can be set in a variety of different possible ways. For example, the update rate can be set by the rate of update of the gas concentration measurement device 504; or can be controlled by the host controller 505; or can be controlled by the pulse mole amount control processor 511 (or a separate processor in communication with it), either at a fixed rate or at rate that is adjusted based on the pulse duration period provided by the host controller 505. In one example, the pulse mole amount control processor 511 sets the update rate as a multiple of 10 times the pulse frequency determined based on the pulse duration period ($\Delta t$) provided by the host controller 505, and communicates that update rate to the gas concentration measurement device 504. Alternatively, for example, the gas concentration measurement device 504 can be selected in advance to have an update rate 504 that is sufficiently high to be in excess of a criterion, such as a 10 times multiple of the maximum expected pulse frequency.

The pulse gas delivery system 506 can further include a heater 519 configured to maintain at least part of the flow of the process gas at an elevated temperature. As discussed above, the precursor gases or other process gases are typically generated by a chemical or physical process that is ongoing during gas delivery, such as by evaporating a liquid or solid. It can therefore be advantageous to use a heater 519 to maintain part or all of the flow of the process gas at a temperature that keeps the process gas in its gaseous state, so that the process gas does not revert to solid or liquid state by cooling as the gas flows through the system. The heater 519 can heat one or more components through which the process gas flows, such as the gas source 501, gas concentration measurement device 504, flow sensor 507, and internal valve 513, and the gas flow lines that flow the gas between those components and to the process chamber 512. In one example, the system uses the heater 519 to heat the gas concentration measurement device 504, the flow sensor 507, and the internal valve 513. The temperature can, for example, be maintained at higher than 150 C, such as 200 C or higher, for example about 230 C. The heater 519 can be used to avoid cold spots along the gas flow path, and can, for example, be used to maintain a substantially constant elevated temperature along the gas flow path, or along at least part of the gas flow path between the gas source 501 and the process chamber 512. By "substantially constant," it is intended that the elevated temperature can, for example, be maintained within a range of within plus or minus 20 C of a maintained temperature, such as within plus or minus 10 C. or within plus or minus 5 C, of the maintained temperature. The heater 519 can be an active or passive heating element, and can be mounted in thermal conductive relationship with one or more of the components that it heats, such as the gas source 501, gas concentration measurement device 504, flow sensor 507, and internal valve 513, and the gas flow lines that flow the gas between those components and to the process chamber 512, or on all of those components. The heater 519 can be internal to the pulse gas delivery system 506, or external to it, or both internal and external to it. In addition, the temperature of the heater 519 can be controlled by a heater control processor 517, which can be controlled by (or can be a portion of) the pulse mole amount control processor 511. For example, the heater control processor can receive temperature information from a temperature sensor 521 located in thermal sensing arrangement with the heater 519 or with any of the components that it heats, or with other components of the system. Based on the temperature information, the heater control processor 517 can provide signals to the heater 519 to adjust the degree or location of heating provided to one or more components.

Figure 6:
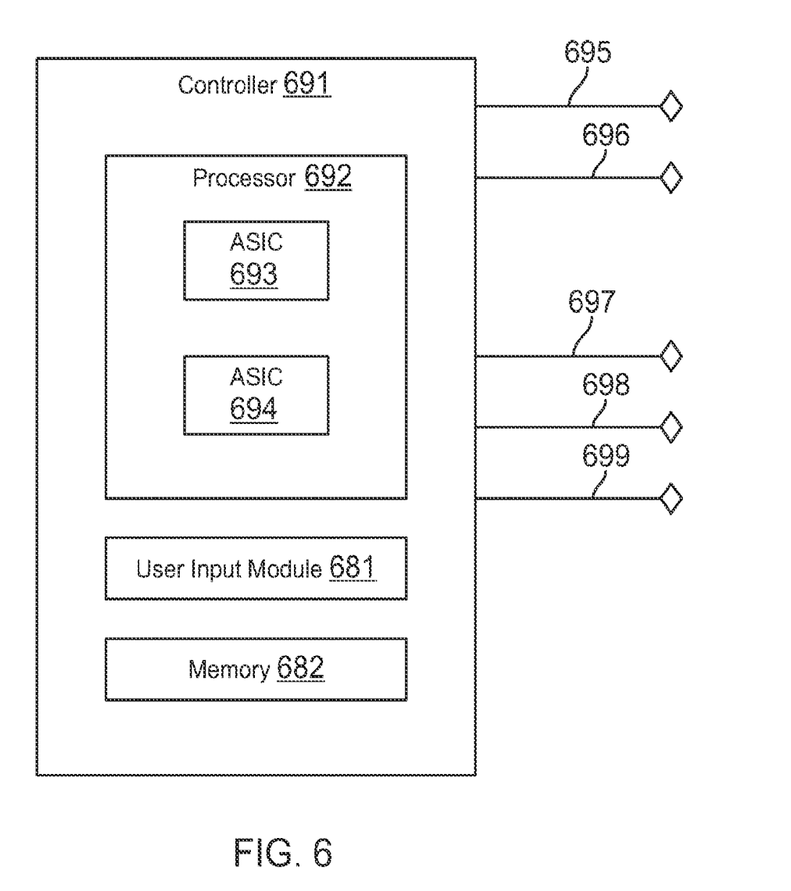
FIG. 6 is a simplified schematic block diagram of a controller that can be used as such components, including, for example, as the pulse mole amount control processor of FIG. 5.

Various techniques set forth herein are implemented using a controller, and can include computer implemented components, such as pulse mole amount control processor 511, flow rate control processor 509, and heater control processor 517 (see FIG. 5). FIG. 6 is a simplified schematic block diagram of a controller that can be used as such components, including, for example, as the pulse mole amount control processor 511 of FIG. 5. Control techniques discussed herein can be implemented using hardware, such as a controller 691 that includes one or more processors 692, which can for example include one or more Application Specific Integrated Circuits (ASICs) 693, 694; application software running on one or more processors 692 of the controller 691; and sensor and/or actuator lines 695-699 delivering electronic signals to and from systems set forth herein (such as gas concentration measurement device 504, host controller 505, flow rate control processor 509, flow sensor 507, internal valve 513, heater control processor 517, heater 519, and temperature sensor 521 of FIG. 5), in which the signals can deliver electronic signals to and from actuated components within systems set forth herein (such as actuator lines delivering electronic signals to actuated valves or other controlled components). The controller 691 can also include user input module 681, which can include components (such as a keyboard, touch pad, and associated electronics in connection with the processor 692 and memory 682) to receive user input such as set points. The controller 691 can also include a memory 682 to store information, and to implement procedures under control of computer hardware and software. It will be appreciated that other control hardware may be used, including control hardware that is at least in part pneumatic.

Portions of the above-described methods and systems can be implemented using one or more computer systems, for example to permit pulse gas delivery with concentration measurement. For example, techniques can be implemented using hardware, software or a combination thereof. When implemented in software, the software code can be executed on any suitable processor or collection of processors, whether provided in a single computer or distributed among multiple computers. For example, the pulse mole amount controller processor 511, flow rate control processor 509, and heater control processor 517 can be provided in a single component, or distributed amongst multiple components.

Advantages of embodiments can, for example, include the ability to provide a precise mole amount of a precursor or other process gas in each gas pulse delivery. The method and apparatus can be applied to a variety of different processes, including Atomic Layer Deposition (ALD) and Atomic Layer Etch (ALE) processes, that have precursors or other process gases in a mixture. Further, the method and apparatus can be applied where the concentration of the precursor or process gas varies during the process, including where the variation of the precursor is wide. The control can be fast, without the need to control blending of gases or the chemistry or physics of a reaction. The method and apparatus is integrated, and simplifies process monitoring and control.

As used herein, the terms "gas" or "gases" include the terms "vapor" or "vapors." should those terms be considered to be different.

As used herein, a "process gas" can be or include a precursor gas, and can also be or include any of a wide variety of other possible gases used in a process, including any pulsed gas mixtures regardless of whether they are precursor gases. For example, in one embodiment, a pulsed WF6 gas mixture can be used. The process in which the process gas is used can, for example, be an Atomic Layer Deposition (ALD) process, an Atomic Layer Etch (ALE) process, a Through Silicon Via (TSV) process, a pulsed deep reactive ion etch (DRIE) process, a plasma enhanced chemical vapor deposition (CVD) process, a plasma enhanced etching process or any process requiring a pulsed gas mixture. The process can, for example, be part of a semiconductor manufacturing process, but can also be used in other processes.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A pulse gas control system, the system comprising:
   a gas concentration measurement system configured to measure a concentration of a process gas in a gas mixture;
   a pulse gas delivery system including a sensor to sense flow of the gas mixture and a control valve to regulate flow of the gas mixture to a flow setpoint during a pulse duration period, the pulse gas delivery system receiving the measured concentration of the process gas in the gas mixture, measured by the gas concentration measurement system, and adjusting the flow setpoint, during the pulse duration period, based on a changed measured concentration during the pulse duration period to control an amount of gas mixture delivered in a pulse of gas flow, based on the measured concentration of the process gas, to control a mole amount of the process gas delivered to a process chamber during the pulse duration period;

the pulse gas delivery system maintaining a constant pulse duration while adjusting the flow setpoint over time during the pulse duration period until the pulse duration period is complete and a total process gas mole delivery per pulse setpoint is reached, the adjusting comprising adjusting the flow setpoint over time during the pulse duration period based on the remaining time within the pulse and the remaining mole amount of process gas to be delivered within the pulse out of the total process gas mole delivery per pulse setpoint; and a heater configured to maintain at least part of the flow of the gas mixture comprising the process gas at an elevated temperature.

2. The system of claim 1, wherein the pulse gas delivery system sets an initial target flow setpoint of the gas mixture in inverse proportion to the received concentration of the process gas.

3. The system of claim 2, wherein the pulse gas delivery system sets the initial target flow setpoint in proportion to a process gas mole delivery per pulse setpoint divided by a product of a pulse duration period multiplied by the received concentration of the process gas.

4. The system of claim 1, wherein the pulse gas delivery system adjusts the flow setpoint based on a relationship:

$$Q_{sp}(t) = \frac{k \cdot M_{sp} - \int_{t_0}^{t} Q_m(t)C(t)dt}{(\Delta t - (t - t_0)) \cdot C(t)}$$

where $Q_{sp}(t)$ is the flow setpoint, k is a mole to flow unit conversion constant, $M_{sp}$ is a process gas mole delivery per pulse setpoint, $Q_m(t)$ is a measured flow rate of the pulse gas delivery system, C(t) is the received process gas concentration, $\Delta t$ is the pulse duration period, t is a current time, and $t_0$ is an initial time of the pulse duration period.

5. The system of claim 1, wherein the gas concentration measurement system comprises an optical gas sensor, a surface acoustic wave device, an ultrasound sensor, a mass spectrometer or a thermal conductive detector.

6. The system of claim 1, wherein the gas concentration measurement system is arranged in series between a source of the gas mixture and the pulse gas delivery system, to receive the gas mixture from a source and to provide the gas mixture to the pulse gas delivery system.

7. The system of claim 1, wherein the gas concentration measurement system is arranged to receive a sample of the gas mixture from a sample line that samples a gas flow of the gas mixture from a source to the pulse gas delivery system.

8. The system of claim 1, wherein the process chamber to which the pulse gas delivery system is configured to deliver the process gas is one of: an Atomic Layer Deposition (ALD) process, an Atomic Layer Etch (ALE) process, a Through Silicon Via (TSV) process, a pulsed deep reactive ion etch (DRIE) process, a plasma enhanced chemical vapor deposition (CVD) process and a plasma enhanced etching process.

9. The system of claim 1, wherein the pulse gas delivery system is configured to receive the concentration of the process gas in the gas mixture at an update rate that is at least ten times a pulse frequency that corresponds to a pulse duration period of the pulse gas delivery system.

10. The system of claim 1, wherein the pulse gas delivery system is configured to control the heater to maintain a substantially constant elevated temperature of the process gas along at least part of the flow of the gas mixture between a source and the process chamber.

11. A method of controlling a pulse gas delivery system, the method comprising:

measuring a concentration of a process gas in a gas mixture using a gas concentration measurement system;

with the pulse gas delivery system, receiving the measured concentration of the process gas in the gas mixture, the pulse gas delivery system including a sensor to sense flow of the gas mixture and a control valve to regulate flow of the gas mixture to a flow setpoint during a pulse duration period; and adjusting the flow setpoint, during the pulse duration period, based on a changed measured concentration during the pulse duration period to control an amount of gas mixture delivered in a pulse of gas flow by the pulse gas delivery system, based on the measured concentration of the process gas, to control a mole amount of the process gas delivered to a process chamber during the pulse duration period;

maintaining a constant pulse duration while adjusting the flow setpoint over time during the pulse duration period until the pulse duration period is complete and a total process gas mole delivery per pulse setpoint is reached, the adjusting comprising adjusting the flow setpoint over time during the pulse duration period based on the remaining time within the pulse and the remaining mole amount of process gas to be delivered within the pulse out of the total process gas mole delivery per pulse setpoint; and using a heater to maintain at least part of the flow of the gas mixture comprising the process gas at an elevated temperature.

12. The method of claim 11, comprising setting an initial target flow setpoint of the gas mixture in inverse proportion to the received concentration of the process gas.

13. The method of claim 12, comprising setting the initial target flow setpoint in proportion to a process gas mole delivery per pulse setpoint divided by a product of a pulse duration period multiplied by the received concentration of the process gas.

14. The method of claim 11, comprising adjusting the flow setpoint based on a relationship:

$$Q_{sp}(t) = \frac{k \cdot M_{sp} - \int_{t_0}^{t} Q_m(t)C(t)dt}{(\Delta t - (t - t_0)) \cdot C(t)}$$

where $Q_{sp}(t)$ is the flow setpoint, k is a mole to flow unit conversion constant, $M_{sp}$ is a process gas mole delivery per pulse setpoint, $Q_m(t)$ is a measured flow rate of the pulse gas delivery system, C(t) is the received process gas concentration, $\Delta t$ is the pulse duration period, t is a current time, and $t_0$ is an initial time of the pulse duration period.

15. The method of claim 11, comprising measuring the concentration of the process gas in the gas mixture using an optical gas sensor, a surface acoustic wave device, an ultrasound sensor, a mass spectrometer or a thermal conductive detector.

16. The method of claim 11, comprising using the pulse gas delivery system to deliver the process gas to one of: an Atomic Layer Deposition (ALD) process, an Atomic Layer Etch (ALE) process, a Through Silicon Via (TSV) process, a pulsed deep reactive ion etch (DRIE) process, a plasma enhanced chemical vapor deposition (CVD) process and a plasma enhanced etching process.

17. The method of claim 11, comprising receiving the concentration of the process gas in the gas mixture at an update rate that is at least ten times a pulse frequency that corresponds to a pulse duration period of the pulse gas delivery system.

18. The method of claim 11, comprising controlling the heater to maintain a substantially constant elevated temperature of the process gas along at least part of the flow of the gas mixture between a source and the process chamber.

19. A pulse gas control system, the system comprising:
a gas concentration measurement system configured to measure a concentration of a process gas in a gas mixture;
a pulse gas delivery system configured to sense flow of the gas mixture and control flow of the gas mixture and to receive the concentration of the process gas in the gas mixture, measured by the gas concentration measurement system, and to control an amount of gas mixture delivered in a pulse of gas flow, based on the received concentration of the process gas, to control a mole amount of the process gas delivered to a process chamber in the pulse;
wherein the pulse gas delivery system is configured to adjust a flow setpoint of the gas mixture during the pulse based on the received concentration of the process gas, and the pulse gas delivery system sets an initial target flow setpoint of the gas mixture in inverse proportion to the received concentration of the process gas;
wherein the pulse gas delivery system sets the initial target flow setpoint in proportion to a process gas mole delivery per pulse setpoint divided by a product of a pulse duration period multiplied by the received concentration of the process gas; and
a heater configured to maintain at least part of the flow of the gas mixture comprising the process gas at an elevated temperature.

20. The system of claim 19, wherein the pulse gas delivery system is configured to receive the concentration of the process gas in the gas mixture at an update rate that is at least ten times a pulse frequency that corresponds to a pulse duration period of the pulse gas delivery system.

21. The system of claim 19, wherein the pulse gas delivery system is configured to control the heater to maintain a substantially constant elevated temperature of the process gas along at least part of the flow of the gas mixture between a source and the process chamber.

22. A pulse gas control system, the system comprising:
a gas concentration measurement system configured to measure a concentration of a process gas in a gas mixture;
a pulse gas delivery system configured to sense flow of the gas mixture and control flow of the gas mixture and to receive the concentration of the process gas in the gas mixture, measured by the gas concentration measurement system, and to control an amount of gas mixture delivered in a pulse of gas flow, based on the received concentration of the process gas, to control a mole amount of the process gas delivered to a process chamber in the pulse;
wherein the pulse gas delivery system is configured to adjust a flow setpoint of the gas mixture during the pulse;
wherein the pulse gas delivery system adjusts the flow setpoint, during a pulse duration period, based on a changed measurement of the process gas concentration during the pulse duration period, based on a relationship:

$$Q_{sp}(t) = \frac{k \cdot M_{sp} - \int_{t_0}^{t} Q_m(t) C(t) dt}{(\Delta t - (t - t_0)) \cdot C(t)}$$

where $Q_{sp}(t)$ is the flow setpoint, k is a mole to flow unit conversion constant, $M_{sp}$ is a process gas mole delivery per pulse setpoint, $Q_m(t)$ is a measured flow rate of the pulse gas delivery system, C(t) is the received process gas concentration, $\Delta t$ is the pulse duration period, t is a current time, and $t_0$ is an initial time of the pulse duration period; and
a heater configured to maintain at least part of the flow of the gas mixture comprising the process gas at an elevated temperature.

23. The system of claim 22, wherein the pulse gas delivery system is configured to receive the concentration of the process gas in the gas mixture at an update rate that is at least ten times a pulse frequency that corresponds to a pulse duration period of the pulse gas delivery system.

24. The pulse gas control system of claim 22, wherein the pulse gas delivery system is configured to control the heater to maintain a substantially constant elevated temperature of the process gas along at least part of the flow of the gas mixture between a source and the process chamber.

25. A method of controlling a pulse gas delivery system, the method comprising:
measuring a concentration of a process gas in a gas mixture;
with the pulse gas delivery system, receiving the concentration of the process gas in the gas mixture;
controlling an amount of gas mixture delivered in a pulse of gas flow by the pulse gas delivery system, based on the received concentration of the process gas, to control a mole amount of the process gas delivered to a process chamber in the pulse;
the controlling comprising adjusting a flow setpoint of the gas mixture during the pulse based on the received concentration of the process gas, and setting an initial target flow setpoint of the gas mixture in inverse proportion to the received concentration of the process gas;
the setting of the initial target flow setpoint being in proportion to a process gas mole delivery per pulse setpoint divided by a product of a pulse duration period multiplied by the received concentration of the process gas; and
using a heater to maintain at least part of the flow of the gas mixture comprising the process gas at an elevated temperature.

26. The method of claim 25, comprising receiving the concentration of the process gas in the gas mixture at an update rate that is at least ten times a pulse frequency that corresponds to a pulse duration period of the pulse gas delivery system.

27. The method of claim 25, comprising controlling the heater to maintain a substantially constant elevated temperature of the process gas along at least part of the flow of the gas mixture between a source and the process chamber.

28. A method of controlling a pulse gas delivery system, the method comprising:
measuring a concentration of a process gas in a gas mixture;
with the pulse gas delivery system, receiving the concentration of the process gas in the gas mixture;
controlling an amount of gas mixture delivered in a pulse of gas flow by the pulse gas delivery system, based on the received concentration of the process gas, to control a mole amount of the process gas delivered to a process chamber in the pulse, the controlling comprising adjusting a flow setpoint of the gas mixture during the pulse;
the adjusting the flow setpoint comprising adjusting the flow setpoint, during a pulse duration period, based on a changed measurement of the process gas concentration during the pulse duration period based on a relationship:

$$Q_{sp}(t) = \frac{k \cdot M_{sp} - \int_{t_0}^{t} Q_m(t)C(t)dt}{(\Delta t - (t - t_0)) \cdot C(t)}$$

where $Q_{sp}(t)$ is the flow setpoint, k is a mole to flow unit conversion constant, $M_{sp}$ is a process gas mole delivery per pulse setpoint, $Q_m(t)$ is a measured flow rate of the pulse gas delivery system, C(t) is the received process gas concentration, $\Delta t$ is the pulse duration period, t is a current time, and $t_0$ is an initial time of the pulse duration period; and
using a heater to maintain at least part of the flow of the gas mixture comprising the process gas at an elevated temperature.

29. The method of claim 28, comprising receiving the concentration of the process gas in the gas mixture at an update rate that is at least ten times a pulse frequency that corresponds to a pulse duration period of the pulse gas delivery system.

30. The method of claim 28, comprising controlling the heater to maintain a substantially constant elevated temperature of the process gas along at least part of the flow of the gas mixture between a source and the process chamber.

* * * * *